United States Patent
Baum et al.

(10) Patent No.: US 7,278,195 B2
(45) Date of Patent: *Oct. 9, 2007

(54) METHOD FOR PRODUCING A COATED MEDICAL SUPPORT DEVICE

(75) Inventors: Abraham Baum, Givataim (IL); Elisha Hoch, Rehovot (IL); Israel Schnitzer, Tel Aviv (IL); Lior Kacir, Rehovot (IL); Felix Rabinovich, Rishon Lezion (IL); Reuben Ilia, Beersheva (IL)

(73) Assignee: Israel Aircraft Industries Ltd. (IL)

( * ) Notice: Subject to any disclaimer, the term of this patent is extended or adjusted under 35 U.S.C. 154(b) by 293 days.

This patent is subject to a terminal disclaimer.

(21) Appl. No.: 10/452,987

(22) Filed: Jun. 3, 2003

(65) Prior Publication Data

US 2004/0193256 A1 Sep. 30, 2004

Related U.S. Application Data

(63) Continuation-in-part of application No. 09/465,115, filed on Dec. 16, 1999, now Pat. No. 6,585,759.

(51) Int. Cl.
*B23P 17/00* (2006.01)
*A61F 2/82* (2006.01)

(52) U.S. Cl. ............ 29/419.2; 29/458; 29/527.2; 72/56; 623/1.46; 623/901; 427/2.24

(58) Field of Classification Search .......... 29/458, 29/527.2, 419.2; 72/54, 56; 623/1.18, 1.38, 623/1.42, 1.43, 1.46, 901, 1.45; 427/2.1, 427/2.24

See application file for complete search history.

(56) References Cited

U.S. PATENT DOCUMENTS

| | | | |
|---|---|---|---|
| 4,713,049 A | 12/1987 | Carter | 604/8 |
| 4,787,884 A | 11/1988 | Goldberg | 604/8 |
| 4,820,262 A | 4/1989 | Finney | 604/8 |
| 4,874,360 A | 10/1989 | Goldberg et al. | 604/8 |
| 5,073,694 A | 12/1991 | Tessier et al. | 219/121.7 |
| 5,345,057 A | 9/1994 | Muller | 219/121.71 |
| 5,531,741 A | 7/1996 | Barbacci | 606/15 |
| 5,534,287 A | 7/1996 | Lukic | 427/2.25 |
| 5,548,894 A | 8/1996 | Muto | 29/890.1 |
| 5,707,385 A | 1/1998 | Williams | 606/192 |

(Continued)

OTHER PUBLICATIONS

V.S. Balanethiram, Xiaoyu Hu, Marina Altynova and Glenn S. Daehn "Hyperplasticity: Enhanced Formability at High Rates" Journal of Materials Processing Technology, vol. 45, 1994, pp. 595-600.

(Continued)

*Primary Examiner*—Jermie E. Cozart
(74) *Attorney, Agent, or Firm*—Paul J. Sutton

(57) ABSTRACT

Method for producing a coated medical support device capable of insertion into the body, the method including the procedures of applying a coating to a section of a work-piece, positioning the work-piece in the vicinity of an electromagnetic field generator, and substantially proximate a forming mandrel, inducing electromagnetic forces in the work-piece which accelerate the work-piece toward the forming mandrel, and forming the work-piece to a medical support device, by changing the original physical configuration of the work-piece to a second physical configuration, the forming mandrel having a mandrel physical configuration, the second physical configuration being influenced by the mandrel physical configuration.

11 Claims, 20 Drawing Sheets

U.S. PATENT DOCUMENTS

| | | | | |
|---|---|---|---|---|
| 5,725,548 A | | 3/1998 | Jayaraman | 606/198 |
| 5,767,480 A | | 6/1998 | Anglin et al. | 219/121.69 |
| 5,780,807 A | | 7/1998 | Saunders | 219/121.71 |
| 5,817,126 A | | 10/1998 | Imran | 606/198 |
| 5,826,330 A | | 10/1998 | Isoda et al. | 29/852 |
| 5,843,117 A | | 12/1998 | Alt et al. | 606/194 |
| 5,843,161 A | | 12/1998 | Solovay | 623/1 |
| 5,843,172 A | | 12/1998 | Yan | 623/1 |
| 5,843,175 A | | 12/1998 | Frantzen | 623/1 |
| 5,899,917 A | | 5/1999 | Edwards et al. | |
| 5,972,027 A | * | 10/1999 | Johnson | 623/1.42 |
| 6,153,252 A | | 11/2000 | Hossainy et al. | 427/2.3 |
| 6,379,379 B1 | * | 4/2002 | Wang | 623/1.15 |
| 6,585,759 B1 | * | 7/2003 | Baum et al. | 623/1.18 |
| 6,692,522 B1 | * | 2/2004 | Richter | 623/1.15 |

OTHER PUBLICATIONS

Metals Handbook, $9^{th}$ Ed. vol. 14, Forming and Forging, ASM Electromagnetic Forming International, Metals Park, OH, pp. 644-653.

G.S. Daehn, M. Altynova, V.S. Balanethiram, G. Fenton, M. Padmanabhan, A. Tamhane, and E. Winnard "High-Velocity Metal Forming—An Old Technology Addresses New Problems", JOM, vol. 7, Jul. 1995, pp. 42-45.

* cited by examiner

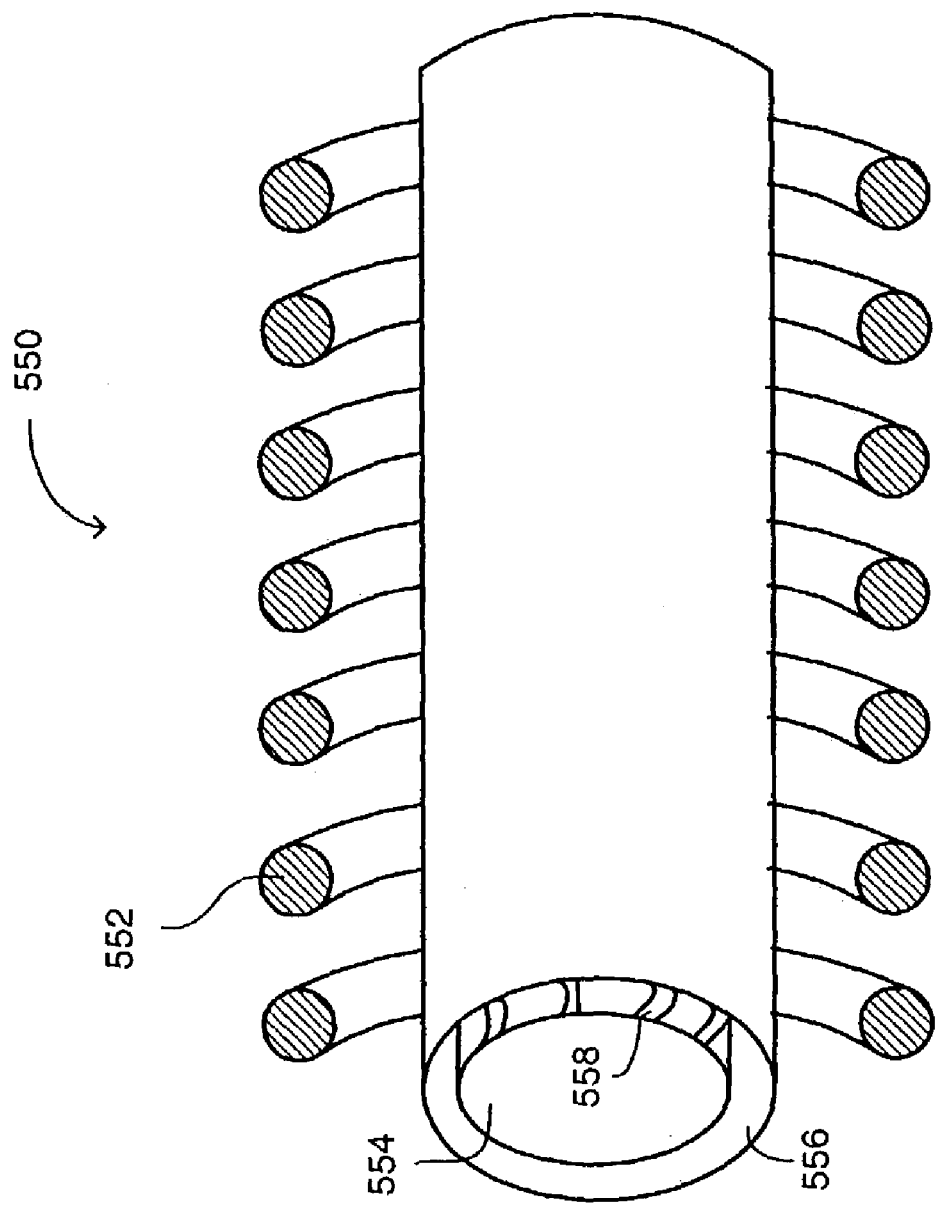

METHOD FOR PRODUCING A COATED MEDICAL SUPPORT DEVICE

This application is a CIP of U.S. patent application Ser. No. 09/465,115 filed Dec. 16, 1999 now U.S. Patent No. 6,585,759.

FIELD OF THE DISCLOSED TECHNIQUE

The disclosed technique relates to a method and apparatus for manufacturing medical devices, in general and to a method and apparatus for manufacturing medical support devices, in particular.

BACKGROUND OF THE DISCLOSED TECHNIQUE

Medical support devices are known in the art. An artery support device is also called a stent. Methods for manufacturing stents are known in the art. U.S. Pat. No. 5,767,480, to Anglin et al., is directed to a hole generation and lead forming for integrated circuit lead frames using laser machining.

U.S. Pat. No. 5,073,694 to Tessier et al., is directed to a method and apparatus for laser cutting a hollow metal work-piece. The method provides for the cutting of the hollow metal work-piece while minimizing or eliminating residue adherence to the inner circumference of the work-piece. Coolant is pumped through the apparatus to contact the inner portion of the work-piece before and during laser cutting.

U.S. Pat. No. 5,345,057 to Muller, is directed to a method of cutting an aperture in a device by-means of a laser beam.

U.S. Pat. No. 5,780,807 to Saunders, is directed to a method and apparatus for direct laser cutting of metal stents. The expandable stent is made from a single length of tubing and utilizes direct laser cutting from a single metal tube using a finely focused laser beam. The stent may be made in a variety of ways, but the preferred method provides for cutting a thin-walled tubular member of materials such as stainless steel in order to remove portions of the tubing and give a desired pattern. This is done by utilizing a laser beam.

U.S. Pat. No. 5,707,385 to Williams, is directed to a drug loaded elastic membrane comprising an expandable sheath for delivering a therapeutic drug in a body lumen. The expandable membrane has a first layer and a second layer, which are joined along their edges to form a fluid-tight seal. Before joining the layers, a plurality of apertures are formed in the first layer by known methods such as using a laser.

U.S. Pat. No. 5,843,117 to Alt et al., is directed to an implantable vascular and endoluminal stent and the process of fabricating the same. Tube-type stent is fabricated from tubing with longitudinally oriented struts coupled together by bars or bridges, which define a plurality of through-holes in the wall of the tube. This multiplicity of through-holes is cut by a laser beam.

U.S. Pat. No. 5,531,741 to Barbacci, is directed to illuminated stents which are designed as an improved light emitting device. The stent is formed by extruding a length of tubing and then followed by molding and shaping. Drainage openings are formed in one step of the process. These holes may be made by piercing the wall of the tubing by utilizing a sharpened cutter or by use of a laser.

Electromagnetic forming (EMF) is known in the art. In general, this method is used to form, cut, pierce, and join metals having relatively high electrical conductivity, such as copper, mild alloy, aluminum, low-carbon steel, brass, and molybdenum. The EMF process uses a capacitor bank, a forming coil, a field shaper (mandrel), and an electrically conductive work-piece to create intense magnetic fields that are used to do useful work. This intense magnetic field, produced by the discharge of a bank of capacitors into a forming coil, lasts only a few microseconds. The resulting eddy currents that are induced in a conductive work-piece that is placed close to the coil, then interact with the magnetic field to cause mutual repulsion between the work-piece and the forming coil. The force of this repulsion is sufficient to stress the work metal beyond its yield strength, resulting in a permanent deformation. The magnetic field rapidly accelerates the work-piece against the mandrel, thus forming it to the desired shape. Because the actual forming takes place in a matter of a few microseconds, the high strain rate forming does not affect the material properties in an adverse way. The pressure induced on the work-piece, is comparable to that encountered in mechanical forming of similar parts.

EMF can be usually applied to five forming methods: compression, expansion, contour forming, punching and joining. It is used to expand, compress, or form tubular shapes, to form a flat sheet, and to combine several forming and assembly operations into a single step. It is used in single-step assembly of metal parts to each other or to other components, such as in electrical cables, and joining of aluminum and copper. Highly resistant metals such as titanium, need special EMF equipment, which operate at higher frequencies in the range of 20 to 100 kHz.

Because the material is loaded into its plastic region, the springback often associated with mechanical forming, is virtually absent in electroformed parts. Joints made by EMF process are typically stronger than the parent material, and compared to other joining methods, such as laser welding. Assemblies using metal parts formed onto plastics, composites, rubber, and ceramics are also common.

More information regarding EMF can be found in the following references: V. S. Balanethiram, Xiaoyu Hu, Marina Altynova and Glenn S. Daehn, "High Velocity forming: Is it Time to Rediscover This Technology", *Engineering Research Center Report ERC/NSM-S-94-15*, The Ohio State University, Columbus, Ohio, 1994, PP. 36-37, V. S. Balanethiram, Xiaoyu Hu, Marina Altynova and Glenn S. Daehn, "Hyperplasticity: Enhanced Formability at High Rates", *Journal of Materials Processing Technology*, Vol. 45, 1994, pp. 595-600, G. S. Daehn, M. Altynova, V. S. Balanethiram, G. Fenton, M. Padmanabhan, A. Tamhane, and E. Winnard, "High-Velocity Metal Forming—An Old Technology Addresses New Problems", JOM, Vol. 7, July 1995, pp. 42-45, and *Metals Handbook*, $9^{th}$ Edition, Volume 14, Forming & Forging, ASM Electromagnetic Forming International, Metals Park, Ohio, pp. 644-653.

U.S. Pat. No. 6,153,252 issued to Hossainy et al., and entitled "Process for Coating Stents" is directed to a method for coating stents in order to prevent the formation of bridges. The stent is placed over a mandrel whose outer diameter is less than the inner diameter of the stent. The stent and the mandrel are dipped into the coating solution. The stent and the mandrel are removed from the coating solution and the coated stent is moved relative to the mandrel. The relative outer diameter of the mandrel and the inner diameter of the stent is such that while the coating is still wet, the movement of the stent along the length of the mandrel, clears the passages of the stent, which remain open after drying.

U.S. Pat. No. 5,534,287 issued to Lukic and entitled "Methods for Applying an Elastic Coating Layer on Stents", is directed to methods for applying a covering layer to an expandable stent, the expandable stent having a discontinuous wall. The covering layer is an elastomeric polymerizable composition. The expandable stent which is in form of a wire mesh, is radially contracted. The inner surface of a tube is coated with a lifting medium, in order to prevent adherence to the covering layer. The expandable stent is inserted into the tube and the expandable stent is allowed to radially expand.

The assembly of the tube and the expandable stent is wetted in the elastomeric polymerizable composition, dissolved in a sufficient amount of solvent, to permit wet forming of a continuous covering layer around the expandable stent. The solvent is evaporated, the elastomeric polymerizable composition is polymerized in the tube and the stent which is covered with the covering layer, is removed from the tube.

SUMMARY OF THE DISCLOSED TECHNIQUE

It is an object of the disclosed technique to provide a novel coated medical support device capable of insertion into the body, and a method for producing the same, which overcome the disadvantages of the prior art. The method includes the procedures of applying a coating to a section of a work-piece, positioning the work-piece in the vicinity of an electromagnetic field generator, and substantially proximate a forming mandrel. The method further includes the procedure of inducing electromagnetic forces in the work-piece which accelerate the work-piece toward the forming mandrel. The method further includes the procedure of forming the work-piece to a medical support device, by changing the original physical configuration of the work-piece to a second physical configuration, wherein the second physical configuration is influenced by a mandrel physical configuration of the forming mandrel.

In accordance with another aspect of the disclosed technique, there is thus provided a medical support device capable of insertion into the body. The medical support device includes an electromagnetically formed work-piece and a coating, which coats at least a section of the work-piece.

The work-piece is formed into a medical support device shape by positioning the work-piece in the vicinity of an electromagnetic field substantially proximate a forming mandrel. The work-piece is further formed by inducing electromagnetic forces in the work-piece and by changing the physical configuration of the work-piece according to the forming mandrel.

BRIEF DESCRIPTION OF THE DRAWINGS

The disclosed technique will be understood and appreciated more fully from the following detailed description taken in conjunction with the drawings in which:

FIG. 10A is an illustration in perspective of a forming device, constructed and operative in accordance with another embodiment of the disclosed technique;

DETAILED DESCRIPTION OF THE EMBODIMENTS

The disclosed technique overcomes the disadvantages of the prior art by providing a novel method for manufacturing medical support devices and elements, using electromagnetic forming (EMF) techniques.

Figure 1:
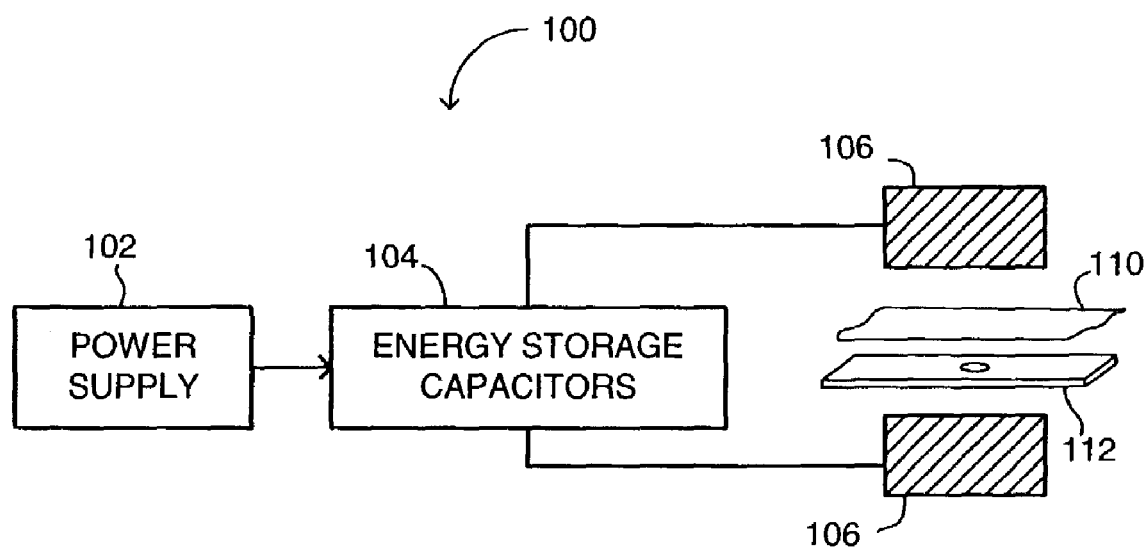
FIG. 1 is a schematic illustration of a system for manufacturing metal medical support elements, constructed and operative in accordance with an embodiment of the disclosed technique.

Reference is now made to FIG. 1, which is a schematic illustration of a system for manufacturing metal medical support elements, generally referenced 100, constructed and operative in accordance with an embodiment of the disclosed technique.

System 100 includes a forming coil 106 (electromagnetic generators), energy storage capacitors 104 and a power supply 102. The energy storage capacitors 104 are coupled with the power supply 102 and with the forming coil—the electromagnetic field generator 106. In the present example, the electromagnetic field generator includes a metal coil.

The forming coil 106 is placed around a conductive metal object, generally referenced 110 and forming coil 106 produces pulses of electromagnetic field. A field shaper mandrel 112 is inserted between the work piece 110 and the coil 106. The electromagnetic generator (forming coil 106) produces pulses of electromagnetic field. This very intense electromagnetic field is produced by the discharge of a bank of capacitors 104 into the forming coil 106. The resulting eddy currents that are induced in the conductive metal object, then interact with the magnetic field to cause mutual repulsion between the conductive metal work-piece 110 and the forming coil 106. The force of this repulsion is sufficient to stress the metal work-piece beyond its yield strength, resulting in a permanent deformation.

The field shaper mandrel 112 is used to concentrate the magnetic field at the points at which the forming/cutting is desired. The magnetic pressure is localized in certain regions of the metal work-piece. This technique most efficiently uses stored energy to produce high local forming pressures in desired areas. In the present example, mandrel 112 includes a hole. Accordingly, apparatus 100 can Electro-Magnetically "punch" a hole in work-piece 110, by accelerating metal work-piece 110 toward the hole bearing mandrel 112.

Figure 2:
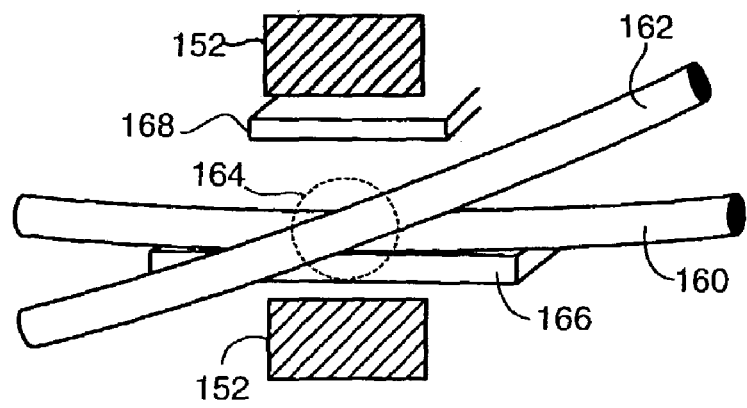
FIG. 2 is an illustration of two wires to be joined together and a forming coil, constructed and operative in accordance with another embodiment of the disclosed technique.

Reference is now made to FIG. 2, which is an illustration of two wires to be joined together and a forming coil, constructed and operative in accordance with another embodiment of the disclosed technique. Wires 162 and 160 are placed one over the other, whereby they cross each other at a crossing section 164. A support member 166 is placed underneath wire 160. An accelerator element 168 can be placed over the crossing section 164. A forming coil 152 is located around the crossing section 164 and the support member 166. At a predetermined moment, the forming coil 152 produces a magnetic field pulse. This electromagnetic field accelerates the two wires, toward the support member 166, thereby forcing them to join at the crossing section 164. At the same time, the magnetic field pulse also accelerates the accelerator element 168 toward the support member 166. Accelerator element 168 can be used in various cases where additional forces are required, such as, when the two joined pieces are characterized by poor conductivity or non at all.

It is noted that the material characteristics of the two wires 162 and 160 are not changed outside the crossing section 164. The strength of the welded joint is at least comparable to the strength of the parent material.

Figure 3A:
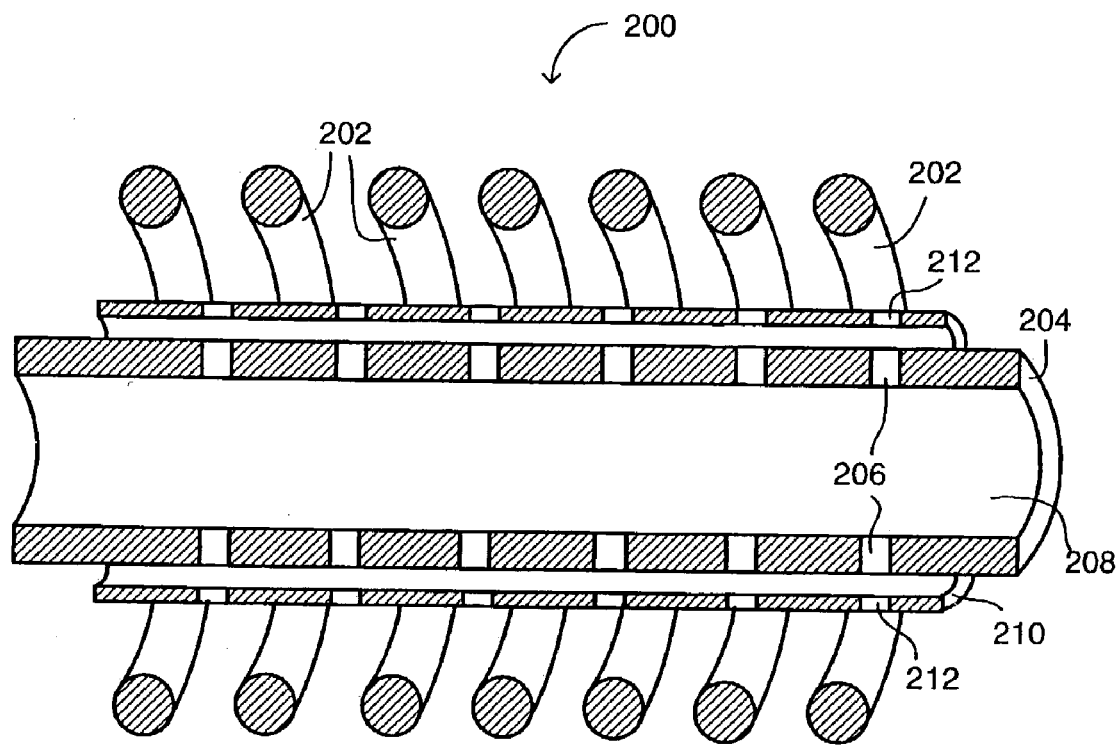
FIG. 3A is a cross sectional illustration of a stent manufacturing device, constructed and operative in accordance with a further embodiment of the disclosed technique.

Reference is now made to FIG. 3A, which is a cross sectional illustration of a stent manufacturing device, generally referenced 200, constructed and operative in accordance with a further embodiment of the disclosed technique. Device 200 includes a mandrel 204 and a coil 202. Mandrel 204 is a general hollow tube (defined by a shaft 208), which includes a plurality of holes 206, at the perimeter thereof. Mandrel 204 is concentrically placed within coil 202. A tubular work-piece 210 is concentrically placed between mandrel 204 and coil 202.

Figure 3B:
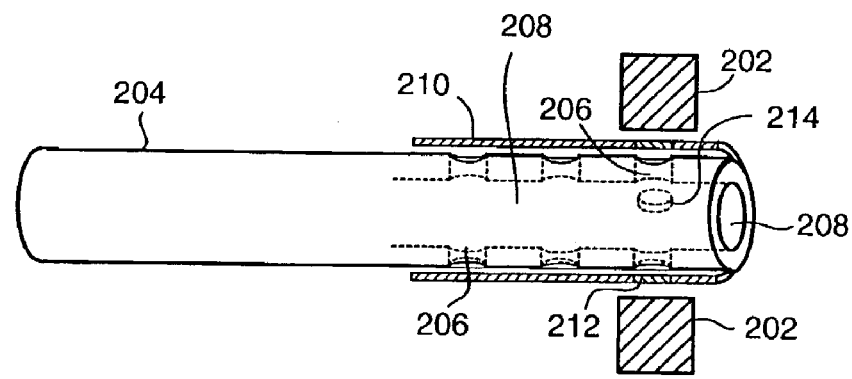
FIG. 3B is a cross sectional view of the stent manufacturing device and the work-piece of FIG. 3A.

Reference is further made to FIG. 3B, which is a cross sectional view of device 200 and work-piece 210 of FIG. 3A. Coil 202 produces an electromagnetic pulse, when an electrical current pulse is conducted there through. This magnetic pulse causes a counter flow of electrical current within the work-piece 210. The vector combination of the electromagnetic field and the counter electric current, causes the generation of mechanical forces on the work-piece 210, which are directed toward the center of mandrel 204.

As a result, pieces (generally referenced 214) of material of the work-piece 210 are sheared against openings 206, thus producing holes 212. In accordance with one aspect of the disclosed technique, the various portions of the work-piece 210 can be punched in a single cycle. Alternatively, the entire work-piece 210 can be punched in a single cycle. It is noted that the material characteristics of the work-piece 210 are substantially maintained throughout and after the punching process. The amount of heat, generated through the process of the disclosed technique is significantly reduced with comparison to other method for manufacturing stents from a single work-piece.

Figure 4A:
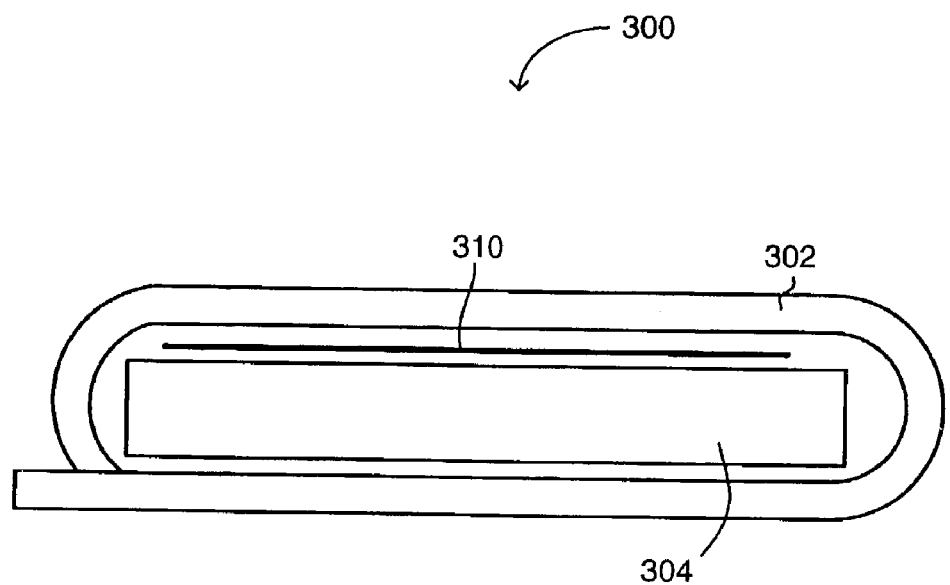
FIG. 4A is a side view illustration of a work-piece, constructed and operative in accordance with another embodiment of the disclosed technique.
Figure 4B:
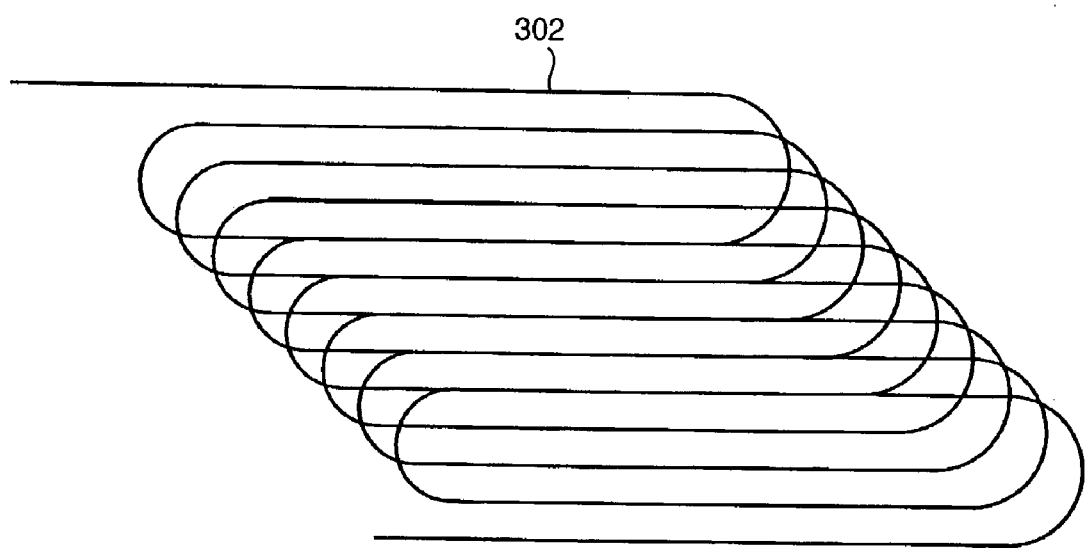
FIG. 4B is an illustration in perspective of the coil of the device of FIG. 4A.
Figure 4C:
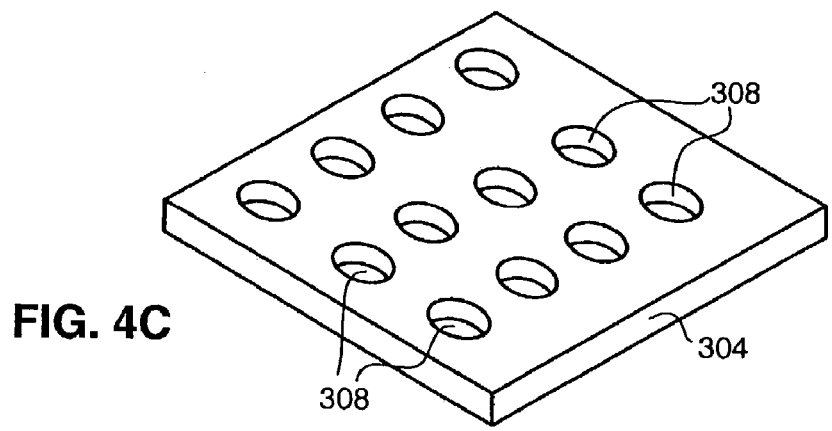
FIG. 4C is an illustration in perspective of the mandrel of the device of FIG. 4A.
Figure 4D:
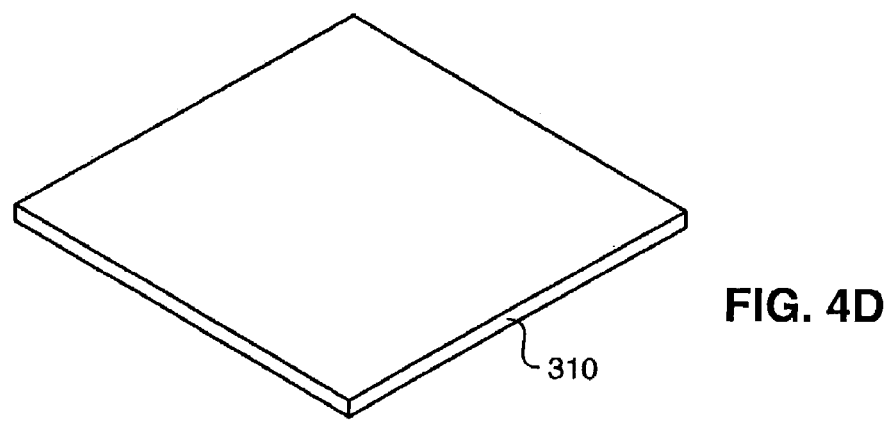
FIG. 4D is an illustration in perspective of the work-piece of FIG. 4A.

Reference is now made to FIGS. 4A, 4B, 4C and 4D. FIG. 4A is a side view illustration of a work-piece, generally referenced 310, and a device, generally referenced 300, for executing a preliminary stage in the manufacturing of a tubular device, constructed and operative in accordance with another embodiment of the disclosed technique. FIG. 4B is an illustration in perspective of the coil of the device of FIG. 4A. FIG. 4C is an illustration in perspective of the mandrel of the device of FIG. 4A. FIG. 4D is an illustration in perspective of the work-piece of FIG. 4A.

Device 300 includes a coil 302 and a mandrel 304. Coil 302 is a flat coil, which is adapted to surround flat objects (FIG. 4B). Mandrel 304 (FIG. 4C) is a flat surface, which includes a plurality of holes, generally referenced 308. Mandrel 304 is placed within coil 302 (FIG. 4A). Work-piece 310 is placed within coil 302, adjacent to mandrel 304. When coil 302 conducts a strong electric pulse, it produces a respective magnetic field pulse, therein. The magnetic field induces electrical current in the work-piece 310, and in turn causes mechanical forces, which drive the work-piece 310 toward mandrel 304. These forces are significantly strong and press the work-piece 310 against mandrel 304. In the present example, these forces cause shearing of work-piece material, where the mandrel 304 exhibits a sharp edge, such as in holes 308.

Figure 4E:
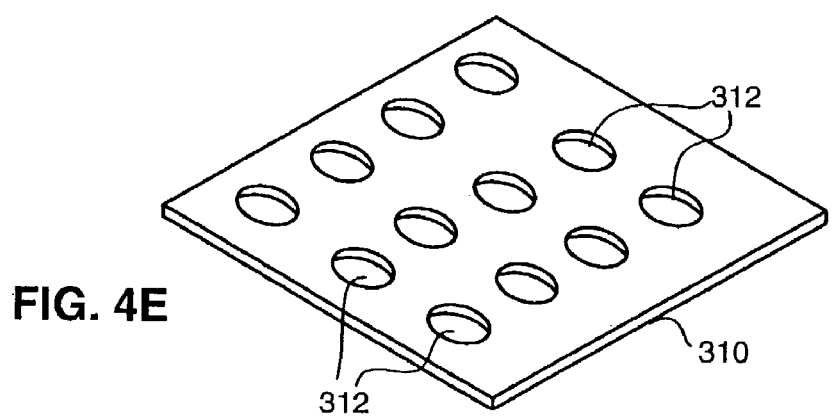
FIG. 4E is an illustration in perspective of work-piece, after being treated by the device of FIG. 4A.

Reference is further made to FIG. 4E, which is an illustration in perspective of work-piece 310, after being treated by device 300. Now, work-piece 310 includes holes, generally referenced 312, in a pattern, which is respective of the hole pattern of mandrel 304. The above device and procedure, provide means for perforating a pattern of holes in a material sheet, which can be further folded, and formed to a shape of a perforated tube. The edges of the material sheet may be joined by metal joining methods known in the art, such as arc welding, gas welding, resistance welding, soldering, brazing, electron beam welding, laser beam welding, friction welding, diffusion bonding, explosive welding, ultrasonic welding, adhesive bonding, EMF forming, and the like.

It is noted that if an accelerating element (as described herein below in connection with FIG. 6) is employed, work-piece 310 can be made of a non-conductive material. Thus, work-piece 310 can be made of a shape memory material, super elastic material as well as stainless steel, alloy, polymeric material, biocompatible material, and the like.

Figure 5:
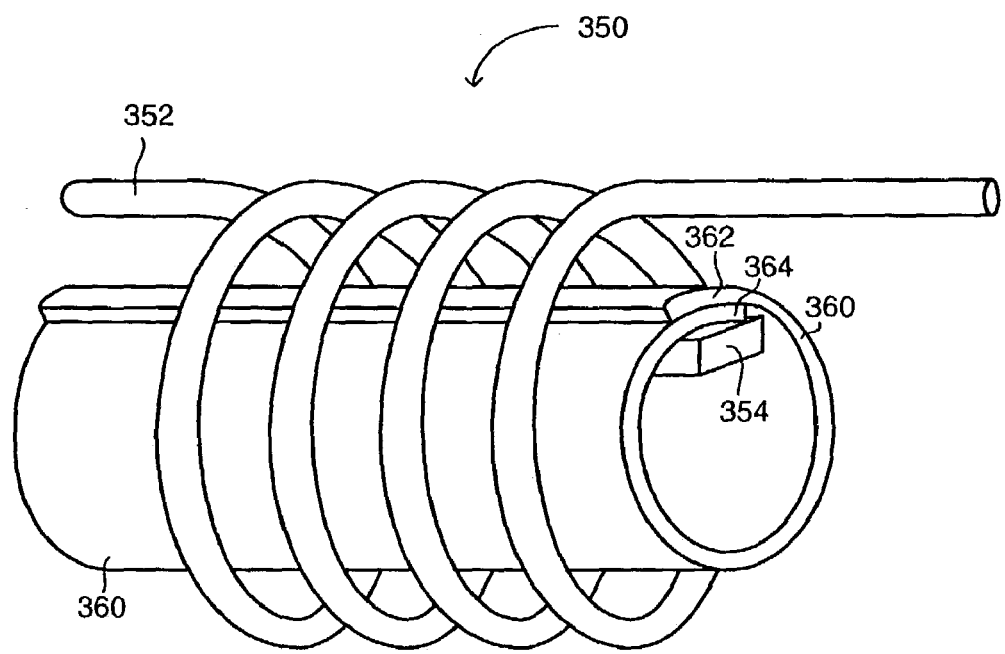
FIG. 5 is an illustration in perspective of a forming device, constructed and operative in accordance with a further embodiment of the disclosed technique.

Reference is now made to FIG. 5, which is an illustration in perspective of a forming device, generally referenced 350, constructed and operative in accordance with a further embodiment of the disclosed technique. Device 350 includes a coil 352 and a mandrel 354. Mandrel 354 is a massive support device, which is fixed to its place. A work-piece 360 made of a generally flat sheet of material, is folded to form a tubular object. Device 350 is designed to firmly couple the overlapping edges 362 and 364 of work-piece 360, thereby producing a closed shape.

Work-piece 360 is inserted in coil 352. Mandrel 354 is inserted inside work-piece 360, and placed in the vicinity of overlapping edges 362 and 364. As a strong pulse of electric current flows through the wire, which includes coil 352, the coil 352 produces a strong magnetic field pulse. This magnetic pulse, causes a counter electric current pulse in work-piece 360. The vector combination of the magnetic pulse and the counter electric current pulse, produce a mechanical force, which accelerates overlapping edges 362 and 364 toward mandrel 354. The strong impact force, causes the two overlapping edges 362 and 364 to join together, thereby producing a closed cylinder.

It is noted that this procedure can be performed on work-pieces, which were treated according to the procedure presented above, in conjunction with FIG. 4A. Alternatively, this procedure can be used independently, for work-pieces, which were initially treated by any other forming technique known in the art. Such techniques include laser beam machining, electrical discharge machining, electrochemical machining, chemical machining, photochemical blanking, abrasive jet machining, abrasive flow machining, ultrasonic machining, hydrodynamic machining, electronic beam machining, stamping, fine blanking, drilling, and the like.

It is noted that the disclosed technique can also be implemented for forming materials, which exhibit poor electrical conductivity or non at all, by utilizing an accelerator element. The accelerator element is made of a highly electrical conductive material, which provides high-induced currents.

Figure 6:
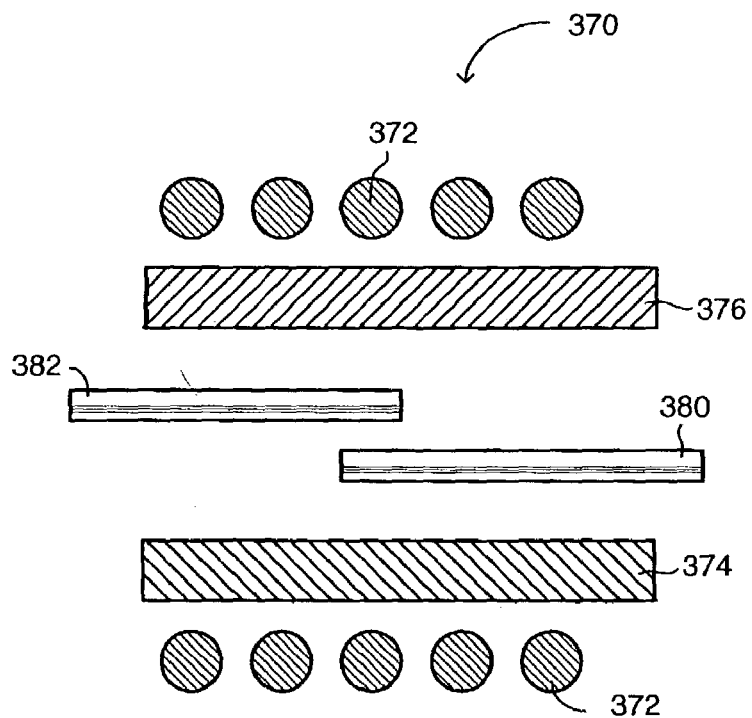
FIG. 6 is a cross-sectional illustration of a forming device, constructed and operative in accordance with another embodiment of the disclosed technique.

Reference is now made to FIG. 6, which is a cross-sectional illustration of a forming device, generally referenced 370, constructed and operative in accordance with another embodiment of the disclosed technique. Device 370 includes a coil 372, a mandrel 374 and an accelerating element 376. Two work-pieces 380 and 382 are inserted in coil 372, overlapping each other.

Figure 7A:
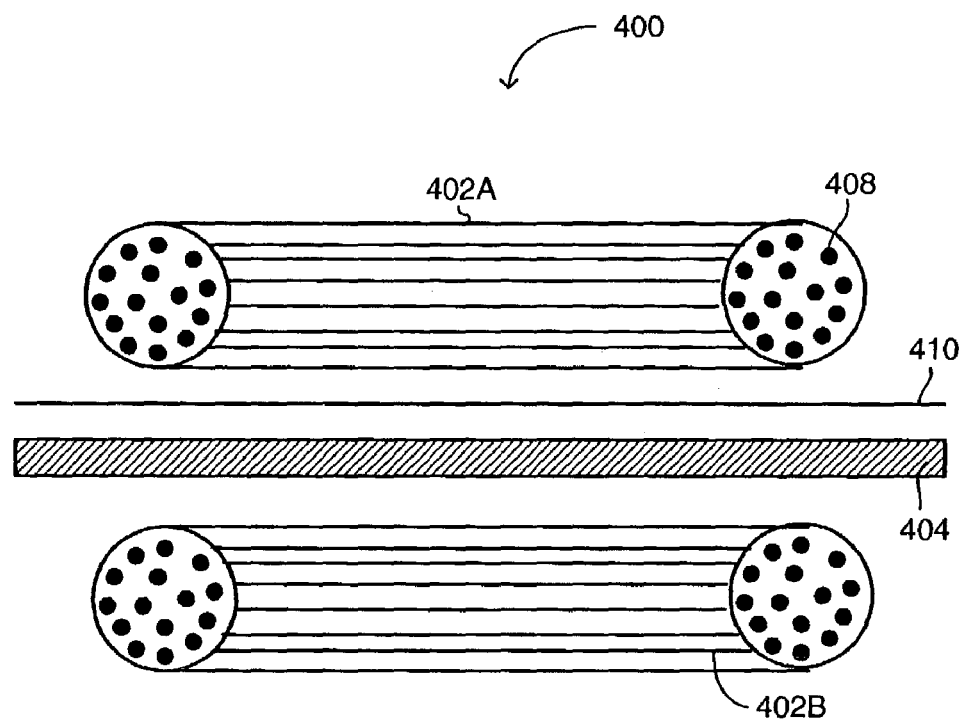
FIG. 7A is a cross-sectional illustration of a forming device, constructed and operative in accordance with a further embodiment of the disclosed technique.
Figure 7B:
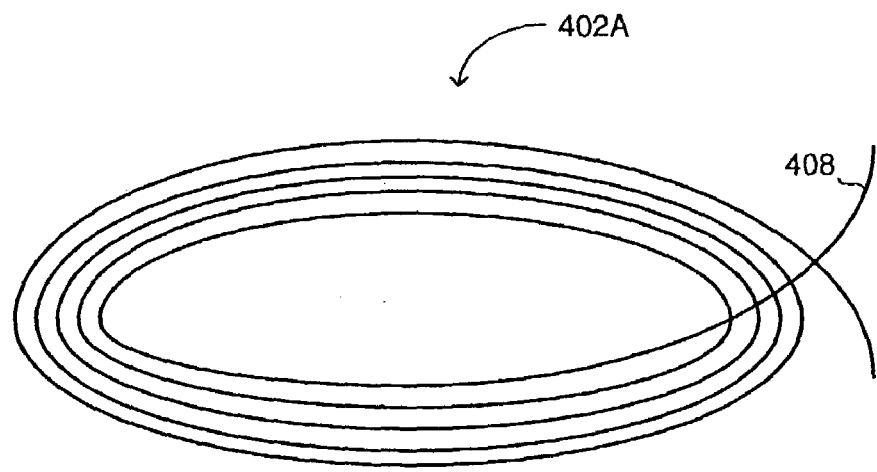
FIG. 7B is an illustration in perspective of a coil of the device of FIG. 7A.

Reference is now made to FIGS. 7A and 7B. FIG. 7A is a cross-sectional illustration of a forming device, generally referenced 400, constructed and operative in accordance with a further embodiment of the disclosed technique. FIG. 7B is an illustration in perspective of a coil of the device of FIG. 7A. Device 400 includes a pair of coils 402A and 402B and a mandrel 404. Coils 402A and 402B each is designed and constructed in the form of a ring.

The coils 402A and 402B are positioned parallel to each other. Mandrel 404 is placed between the coils 402A and 402B. A work-piece 410 is placed between coil 402A and mandrel 404, in close vicinity to coil 402A. When wire 408 conducts an electric current pulse, it produces in turn, a magnetic field pulse, which is induced onto work-piece 410. Work-piece 410 produces a counter electric current. The vector combination of the magnetic field and the counter electric current pulse produces a mechanical force, which accelerates work-piece 410 toward mandrel 404. Work-piece 410 is deformed depending on the shape (curves and openings) which characterizes mandrel 404.

Figure 7C:
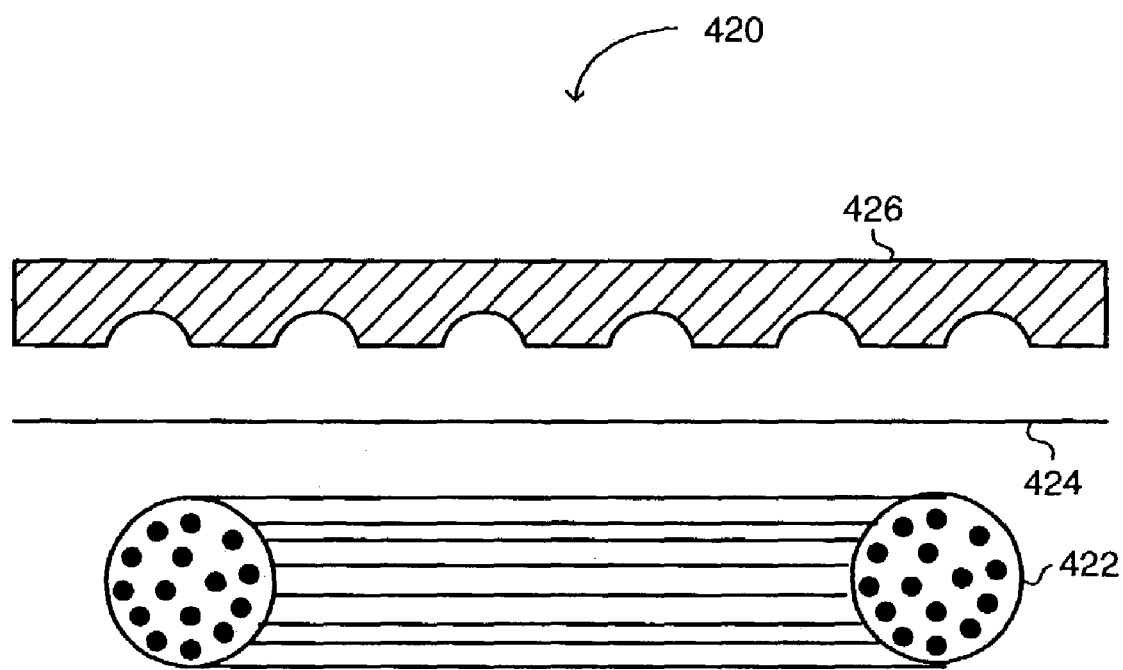
FIG. 7C is a cross-sectional illustration of a forming device, constructed and operative in accordance with another embodiment of the disclosed technique.

Reference is further made to FIG. 7C, which is a cross-sectional illustration of a forming device, generally referenced 420, constructed and operative in accordance with another embodiment of the disclosed technique. Forming device 420 includes a coil 422 similar to coil 402A as described with reference to FIG. 7A, and a mandrel 426. A work-piece 424 is placed between the coil 422 and mandrel 426. Work-piece 424 is deformed depending on the shape (curves and openings) which characterizes mandrel 426, in a process similar to that described with reference to FIG. 7A.

Figure 8:
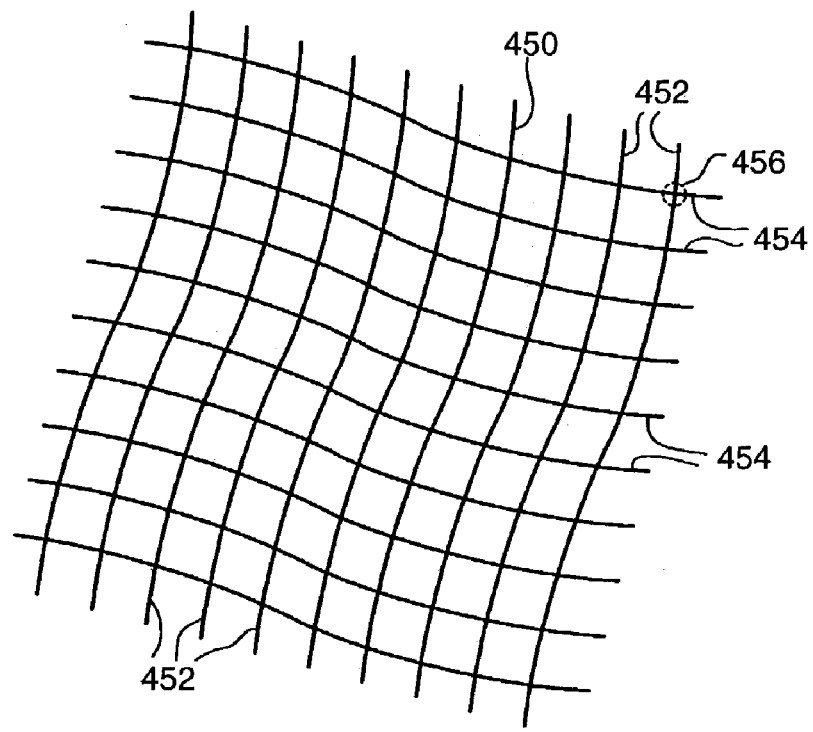
FIG. 8 is a schematic illustration of a metal web, constructed in accordance with a further embodiment of the disclosed technique.

Reference is now made to FIG. 8, which is a schematic illustration of a metal web, generally referenced 450, constructed in accordance with a further embodiment of the disclosed technique. Web 450 is formed from a plurality of wires, generally referenced 452 and 454. These wires are arranged in a crosswise structure, wherein the length portion is made of wires 452, and the breadth portion is made of wires 454. An intersection between a selected length wire 452 and a selected breadth wire 454 is denoted 456. In the present example, the upper right intersection 456 is further denoted by a circle. In accordance with the disclosed technique, each of these intersections, is joined using electromagnetic forming techniques. It is noted that each of the wires 452 and 454 can be made using a different metal or conductive compound material.

For example, the length portion wires can be made of elastic alloys while the breadth portion wires are made of shape memory alloys. It is noted that the use of electromagnetic forming, simplifies the manufacturing process, while maintaining the original characteristics of the materials used, such as elasticity, plasticity, shape memory characteristics, and the like.

Figure 9A:
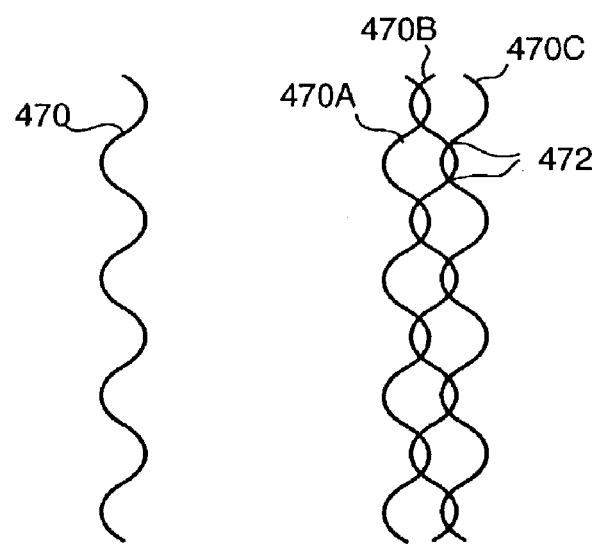
FIG. 9A is a schematic illustration of a plurality of wire elements and a wire structure, constructed and operative in accordance with another embodiment of the disclosed technique.

Reference is now made to FIG. 9A, which is a schematic illustration of a plurality of wire elements, generally referenced 470, and a wire structure, constructed and operative in accordance with another embodiment of the disclosed technique. Wire 470 is shaped, generally as a uniform sinus waveform. Wires 470A, 470B and 470C, being identical to wire 470, form a mesh structure, when placed side by side and joined at selected intersections (generally referenced 472) thereof, by means of electromagnetic forming techniques.

It is noted that similarly to the structure of FIG. 8, various types of material can be used to form each of the wires 470.

Hence, the structure can be made of many different materials. In the present example, wire 470A is made of shape memory material having a two-way action, at two different temperatures, wire 470B is made of shape memory alloy having a one way action, at a predetermined temperature and wire 470C is made of a spring alloy. It is noted that alloys having plastic characteristics can also be used for such wires.

Figure 9C:
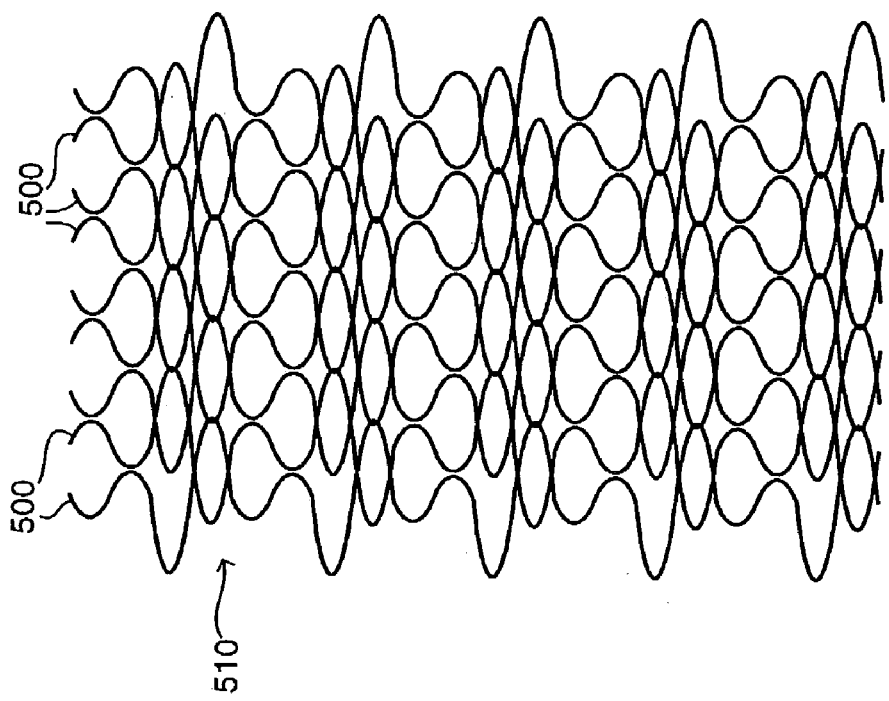
FIG. 9C is an illustration of a mesh structure, constructed in accordance with another embodiment of the disclosed technique.
Figure 9B:
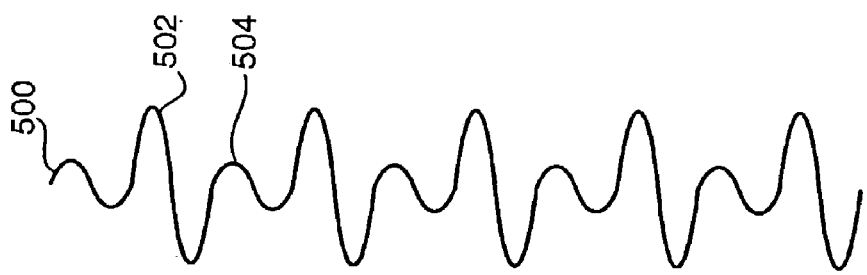
FIG. 9B is an illustration of a wire, constructed in accordance with a further embodiment of the disclosed technique.

Reference is now made to FIGS. 9B and 9C. FIG. 9B is an illustration of a wire, generally referenced 500, constructed in accordance with a further embodiment of the disclosed technique. FIG. 9C is an illustration of a mesh structure, generally referenced 510, constructed in accordance with another embodiment of the disclosed technique.

Wire 500 is shaped as a non-uniform wave function, having "maximum" locations, generally referenced 502 and 504. It is noted that in accordance with further aspects of the disclosed technique, this wave function can include a combination of any known wave function, such as triangle, square, chainsaw, and the like. With reference to FIG. 9C, a plurality of wires 500 are joined together by means of electromagnetic technique, to form mesh structure 510.

Figure 9D:
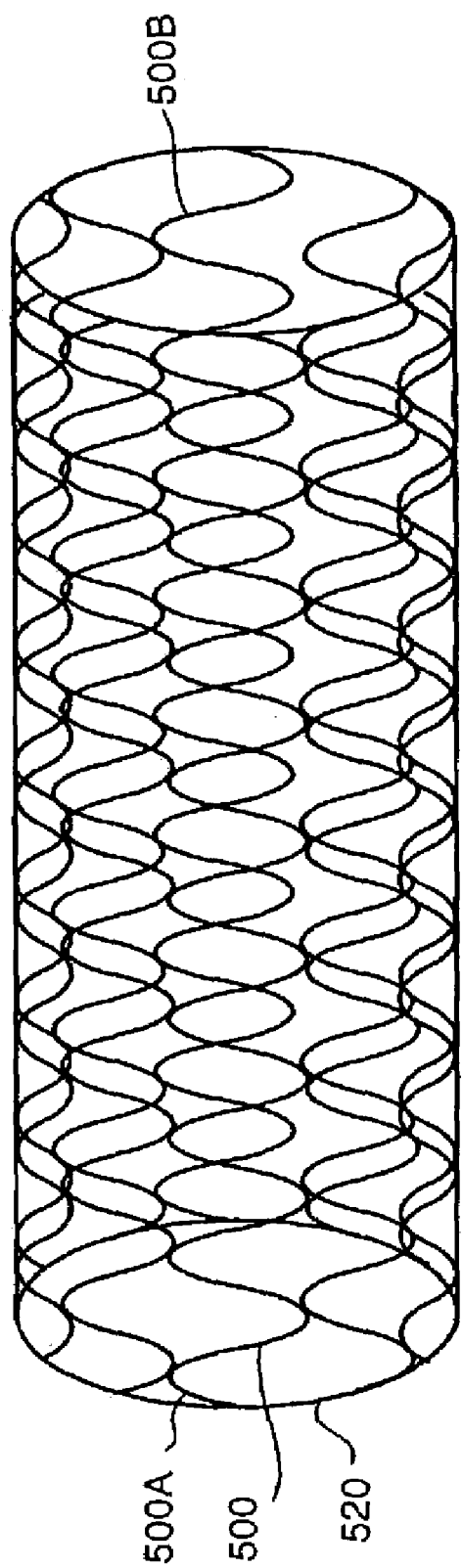
FIG. 9D is an illustration of a medical support device, constructed and operative in accordance with a further embodiment of the disclosed technique.

Reference is further made to FIG. 9D, which is an illustration of a medical support device, generally referenced 520, constructed and operative in accordance with a further embodiment of the disclosed technique. In general, each of the mesh or web structures presented above, can be used to form a medical support device such as a stent or a catheter tip. In the present example, mesh 510 (FIG. 9C) is curved so that the left side meets the right side thereof, thereby forming support device 520. It is noted that the intersections between a left side wire 500A and a right side wire 500B can be fixed together by means of electromagnetic forming techniques, where one electromagnetic coil is placed around the tube mesh, or by any other joining technique, such as laser welding.

Figure 10B:
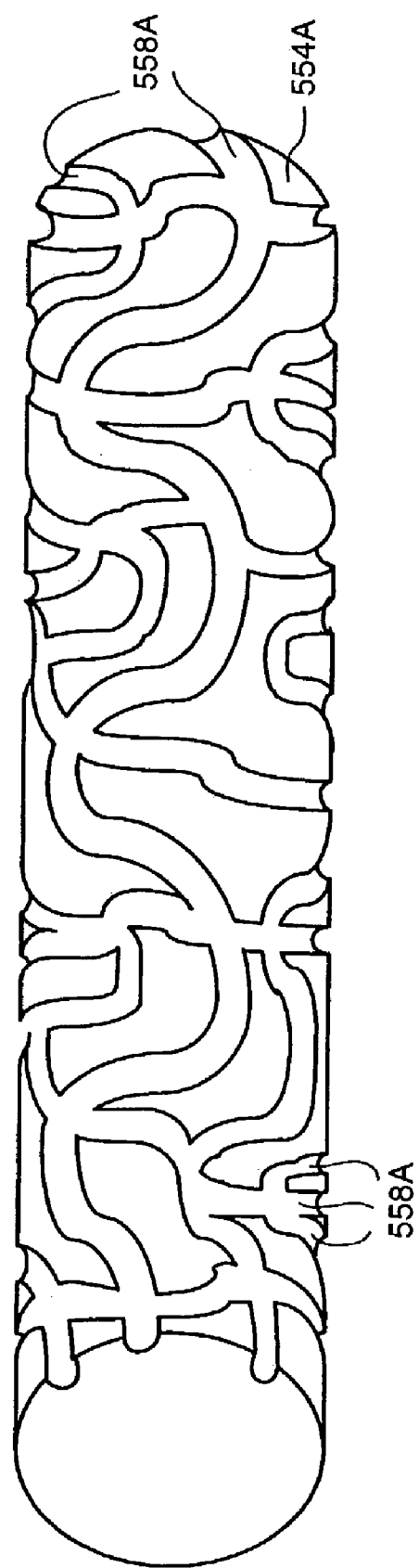
FIG. 10B is an illustration in perspective of a mandrel, for use with the forming device of FIG. 10A, constructed and operative in accordance with a further embodiment of the disclosed technique.
Figure 10C:
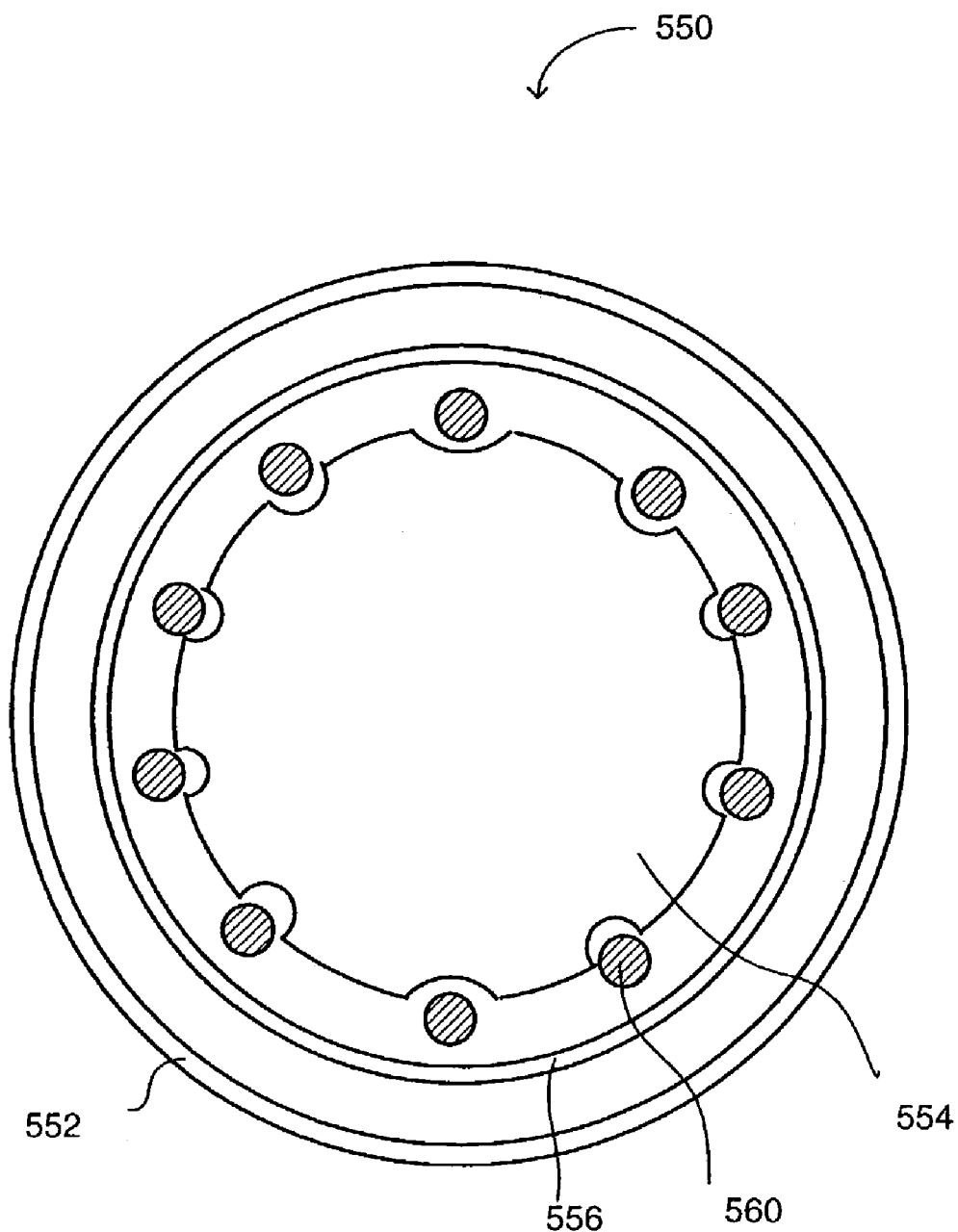
FIG. 10C is a side view of forming device 550 of FIG. 10A.

Reference is now made to FIGS. 10A, 10B, and 10C. FIG. 10A is an illustration in perspective of a forming device, generally referenced 550, constructed and operative in accordance with another embodiment of the disclosed technique. FIG. 10B is an illustration in perspective of a mandrel, generally referenced 554A, for use with the forming device 550 of FIG. 10A, constructed in accordance with a further embodiment of the disclosed technique. FIG. 10C is a side view of forming device 550 of FIG. 10A.

Forming device 550 includes a forming coil 552, a mandrel 554 and a conductive layer 556. Mandrel 554 is adapted to receive a plurality of wires, arrange them in a predetermined structure and hold them together during the forming procedure. With reference to FIG. 10B, mandrel 554A includes a plurality of groves, generally referenced 558A, which define a web like structure. These grooves are then filled with wires and formed within device 550.

Referring both to FIGS. 10A and 10C, a plurality of wires, generally referenced 560 are placed in grooves 558. Mandrel 554 and the inserted wires 560 are wrapped with conductive layer 556, which increases the conductivity of the wire structure. Similar to devices presented herein above, the coil 552 produces a magnetic field pulse as an electric current pulse flows there through. In turn, the combination of conductive layer 556 and wires 560 produce a counter electric current and the combination of the above produces a mechanical force, which bonds the wires together.

In accordance with another aspect of the disclosed technique, a coating is applied to the work-piece and a coated stent is constructed, by forming the coated work-piece with the aid of an electromagnetic field generator. Electromagnetic forming operation does not change any of the properties of the coating, nor does it expose the work-piece to high temperatures. Accordingly, the work-piece can be coated with a variety of coatings, with great ease, before it is formed into a stent. Hence, different types of coatings of different thicknesses can be applied to hard-to-reach surfaces of the stent (e.g., inner surfaces), while substantially eliminating the formation of bridges (i.e., perforations plugged by the coating).

Figure 11A:
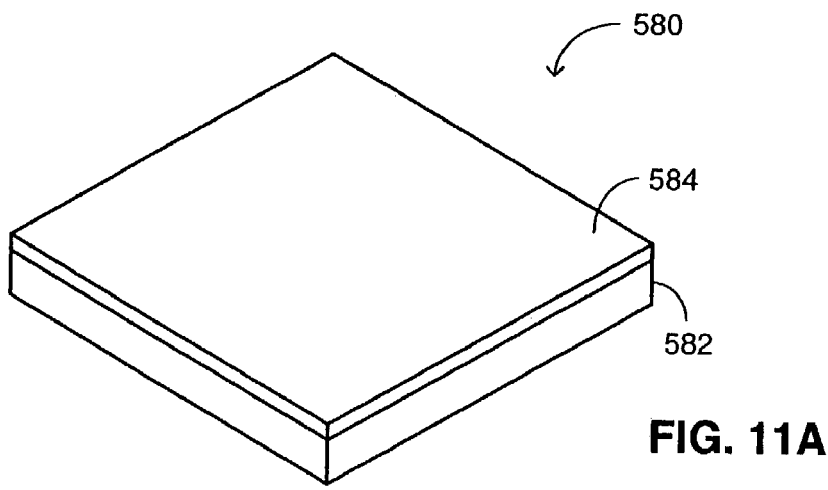
FIG. 11A is an illustration in perspective of a coated work-piece.
Figure 11B:
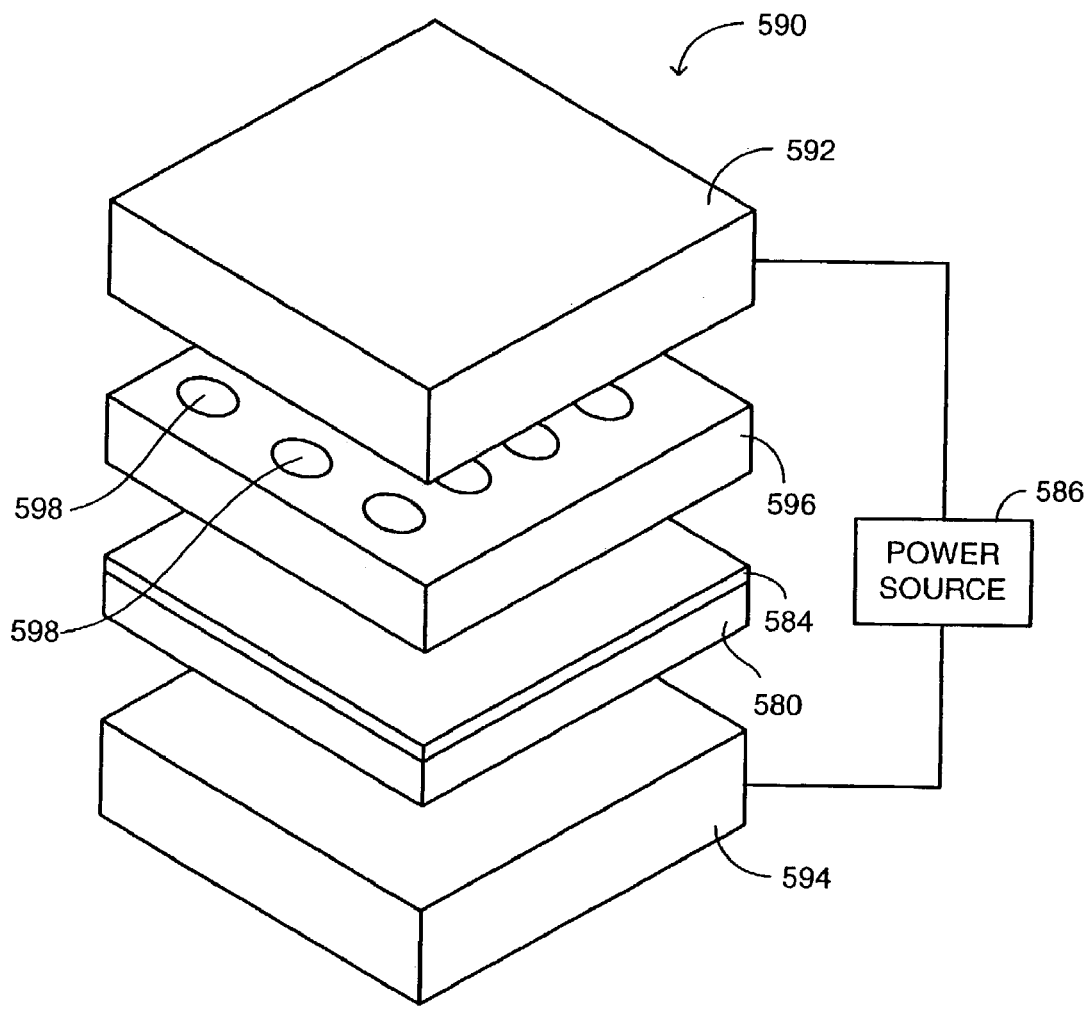
FIG. 11B is an illustration in perspective of a system for forming a plurality of perforations in the coated work-piece of FIG. 11A, constructed and operative in accordance with another embodiment of the disclosed technique.
Figure 11C:
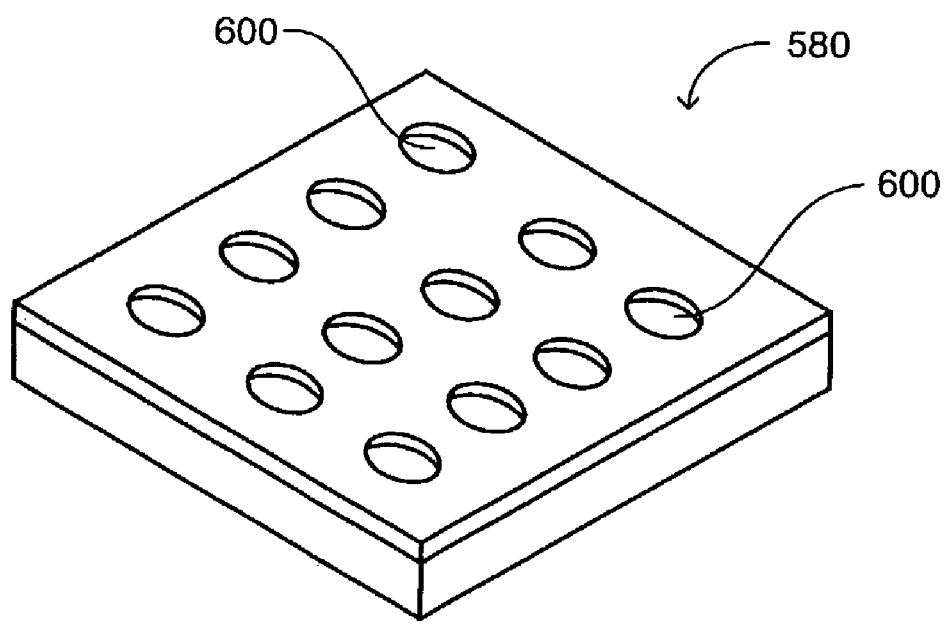
FIG. 11C is an illustration in perspective of the coated work-piece of FIG. 11A, after being formed by the system of FIG. 11B.

Reference is now made to FIGS. 11A, 11B, and 11C. FIG. 11A is an illustration in perspective of a coated work-piece, generally referenced 580. FIG. 11B is an illustration in perspective of a system for forming a plurality of perforations in the coated work-piece of FIG. 11A, generally referenced 590, constructed and operative in accordance with another embodiment of the disclosed technique. FIG. 11C is an illustration in perspective of the coated work-piece of FIG. 11A, after being formed by the system of FIG. 11B.

With reference to FIG. 11A, coated work-piece 580 includes a work-piece 582 and a coating 584. Work-piece 582 is made of either a conductive or a non-conductive material, such as a shape memory material, super elastic material, stainless steel, alloy, polymeric material, biocompatible material, and the like. Coating 584 is made of a substance like bio-degradable polymer or absorbable hydrogel which can release drugs, such as sirolimus, taxol, Actinomycin D, N. O. donors (Nitric Oxide), dexamethasone, heparin, hirudin, iloprost, metallo-proteinase inhibitors, platelet glycoprotein 2b/3a antagonist or genes and cells. Coating 584 can also be made from silicone, silicone carbide, phosphorylcholine, carbide, carbofilm™, titanium-nitride-oxide, expandable polytetrafluorethylene (PTFE) membrane, gold, polyethylene oxide, and the like.

Coating 584 can further be made of a substantially flexible material or, (e.g., gold, complex—titanium nitride oxide or as described above), such that work-piece 582 remains flexible even after applying coating 584 to work-piece 582. When such a coating is applied to a stent, it is possible to deform the coated stent (e.g., expanding, contracting, twisting, bending, compressing and extending).

Coating 584 can be applied to work-piece 582, by methods known in the art, such as by dipping work-piece 582 in a liquid bath, by spraying work-piece 582 (i.e., printing with an inkjet, bubble-jet, and the like), by electrolysis, and the like. Thus, either one side or both sides of the work-piece can be coated with the coating. Moreover, the thickness of coating 584 on work-piece 582 can be controlled in a manner which is particular to the respective method of coating.

With reference to FIG. 11B, system 590 includes two forming coils 592 and 594 similar to forming coils 106 (FIG. 1), coupled with energy storage capacitors (not shown), similar to energy storage capacitors 104 and with a power supply 586, similar to power supply 102. Coated work-piece 580 is placed between coils 592 and 594, and a mandrel 596 similar to mandrel 304 (FIG. 4C), is placed between coil 592 and coated work-piece 580. Mandrel 596 includes a plurality of holes 598.

When an electromagnetic field is generated by coils 592 and 594, selected regions of coated work-piece 580 in the vicinity of holes 598 yield, thereby forming a plurality of holes 600 in coated work-piece 580 (FIG. 11C). It is noted that holes 600 are formed in work-piece 582 as well as in coating 584. The operation of coils 592 and 594 is of short duration, substantially no heat is generated during this operation and substantially no mechanical strain is applied to coating 584. Therefore, the physical properties (e.g., thickness) and chemical properties (e.g., molecular structure) of coating 584 remain substantially constant throughout the forming operation.

It is noted that the coated work-piece can be rolled to a cylinder similar to tubular object 360 (FIG. 5). Then, the two edges of the cylinder can be joined together by employing a forming device similar to forming device 350, thereby constructing a coated tubular object.

Figure 12A:
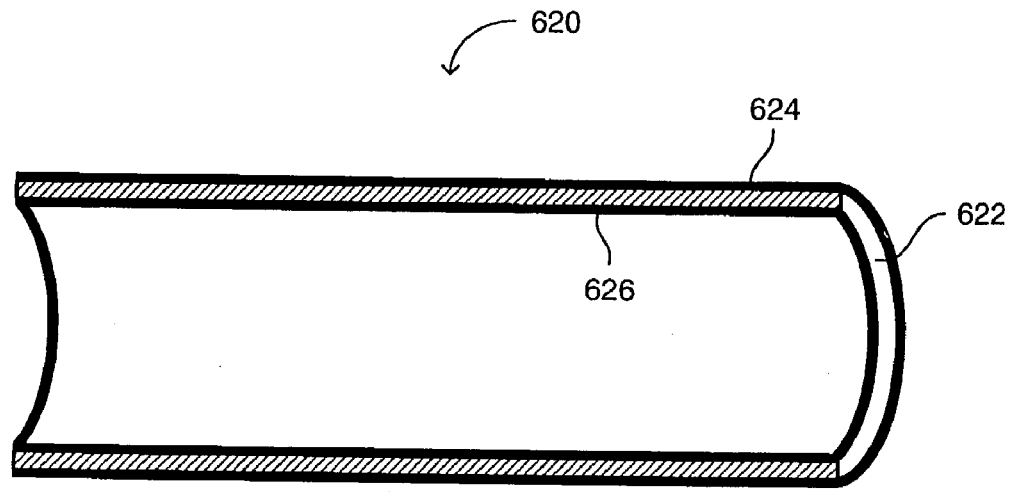
FIG. 12A is an illustration in perspective of a cross section of a coated tubular work-piece.
Figure 12B:
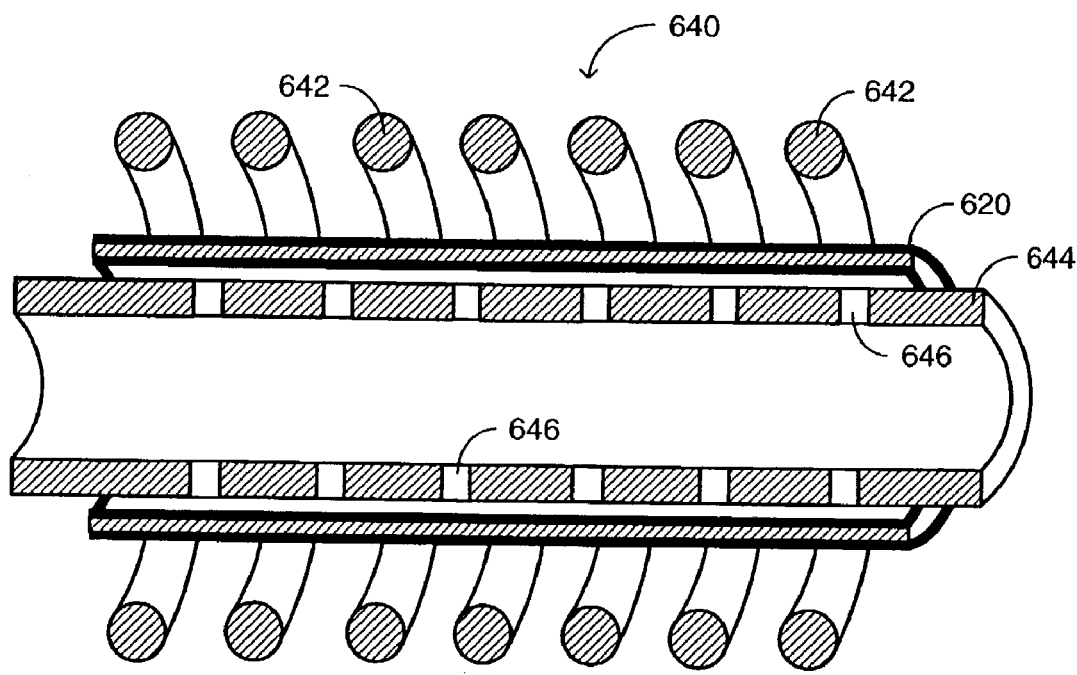
FIG. 12B is an illustration in perspective of a cross section of a system for forming a plurality of perforations in the coated tubular work-piece of FIG. 12A, constructed and operative in accordance with a further embodiment of the disclosed technique.
Figure 12C:
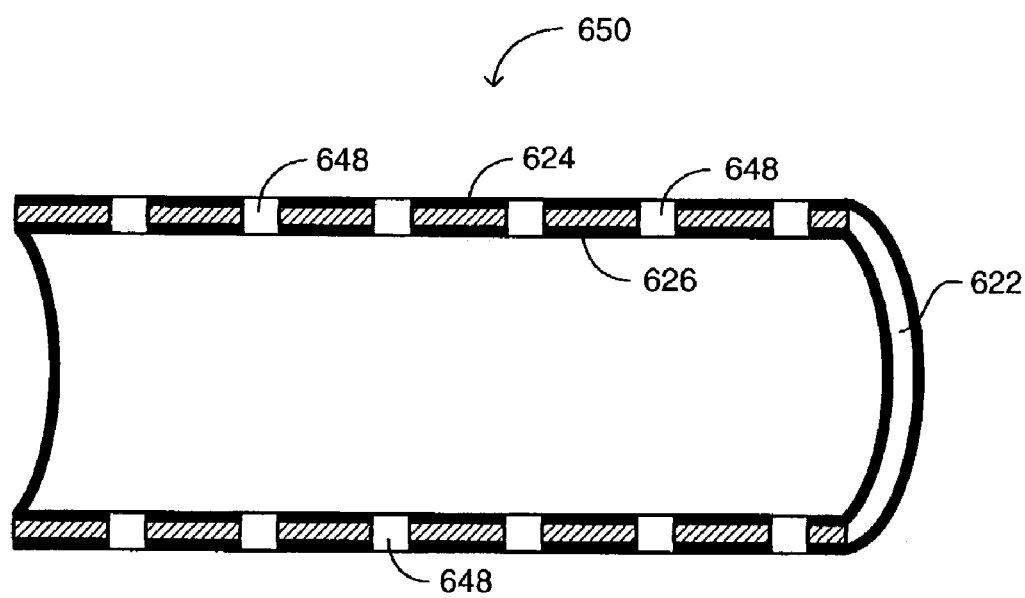
FIG. 12C is an illustration in perspective of a cross section of a coated stent, formed from the coated tubular work-piece of FIG. 12A, by the system of FIG. 12B, in accordance with another embodiment of the disclosed technique.

Reference is now made to FIGS. 12A, 12B, and 12C. FIG. 12A is an illustration in perspective of a cross section of a coated tubular work-piece, generally referenced 620. FIG. 12B is an illustration in perspective of a cross section of a system for forming a plurality of perforations in the coated tubular work-piece of FIG. 12A, generally referenced 640, constructed and operative in accordance with a further embodiment of the disclosed technique. FIG. 12C is an illustration in perspective of a cross section of a coated stent, generally referenced 650, formed from the coated tubular work-piece of FIG. 12A, by the system of FIG. 12B, in accordance with another embodiment of the disclosed technique.

Coated tubular work-piece 620 includes a tubular work-piece 622 and coatings 624 and 626. Coating 624 is applied to an outer surface (not shown) of tubular work-piece 622 and coating 626 is applied to an inner surface (not shown) of tubular work-piece 622. Coatings 624 and 626 can be either the same or different. For example, coating 624 is a substance which prevents intimal proliferation (i.e., restenosis) and coating 626 is a substance which prevents thrombosis (i.e., clotting). The thicknesses of coatings 624 and 626 can be either substantially the same or different.

With reference to FIG. 12B, system 640 includes a coil 642 and a mandrel 644. Coil 642 and mandrel 644 are similar to coil 202 (FIG. 3A) and mandrel 204, respectively. Mandrel 644 includes a plurality of holes 646. The outer diameter (not shown) of mandrel 644 is smaller than the inner diameter (not shown) of coated tubular work-piece 620. Coated tubular work-piece 620 is placed within coil 642 and mandrel 644 is placed within coated tubular work-piece 620.

When an electromagnetic field is generated by coil 642, selected regions of coated tubular work-piece 620 in the vicinity of holes 646 yield, thereby forming a plurality of holes 648 (FIG. 12C) in coated tubular work-piece 620 and forming coated tubular work-piece 620 into a coated stent 650. It is noted that holes 648 are made in tubular work-piece 622, as well as in coatings 624 and 626. Thus, when coated stent 650 is placed inside a lumen of a patient, coatings 624 and 626 gradually dislodge from the outer surface and the inner surface of coated 650, respectively, and are absorbed by the tissue of the patient or the bodily fluids thereof.

Figure 13:
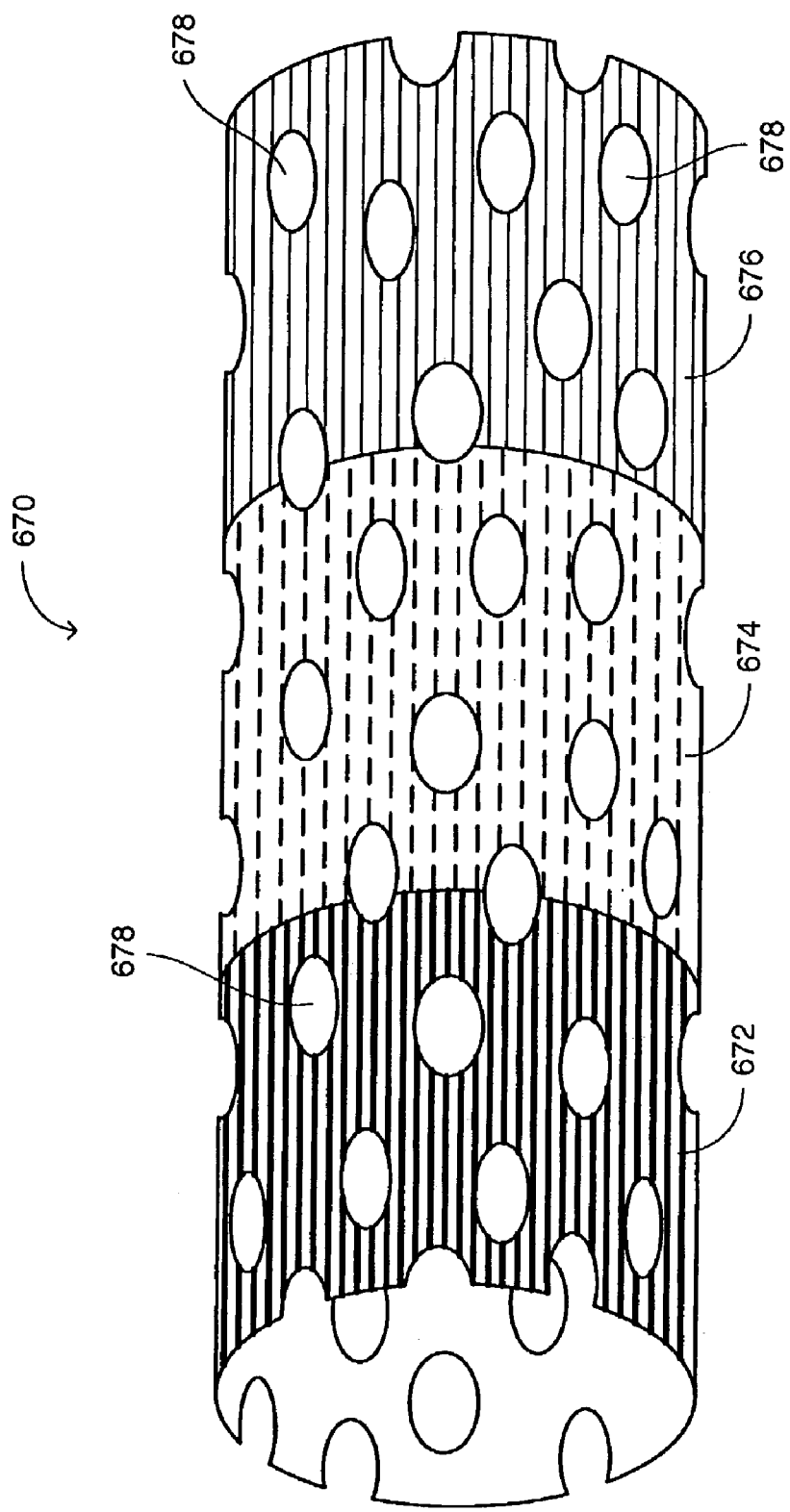
FIG. 13 is an illustration in perspective of a coated stent, constructed and operative in accordance with a further embodiment of the disclosed technique.

Reference is now made to FIG. 13, which is an illustration in perspective of a coated stent, generally referenced 670, constructed and operative in accordance with a further embodiment of the disclosed technique. Coated stent 670 includes a plurality of coatings 672, 674 and 676 on the outer surface (not shown) thereof and a plurality of holes 678.

Coatings 672, 674 and 676 as well as the thicknesses thereof, are different. Thus, when coated stent 670 is placed within the lumen of the patient, a prescribed dose of each of the substances of coatings 672, 674 and 676 is absorbed by the tissue or the bodily fluid of the patient. Alternatively, the inside surface (not shown) of the coated stent can be coated with different coatings at different thicknesses.

Figure 14:
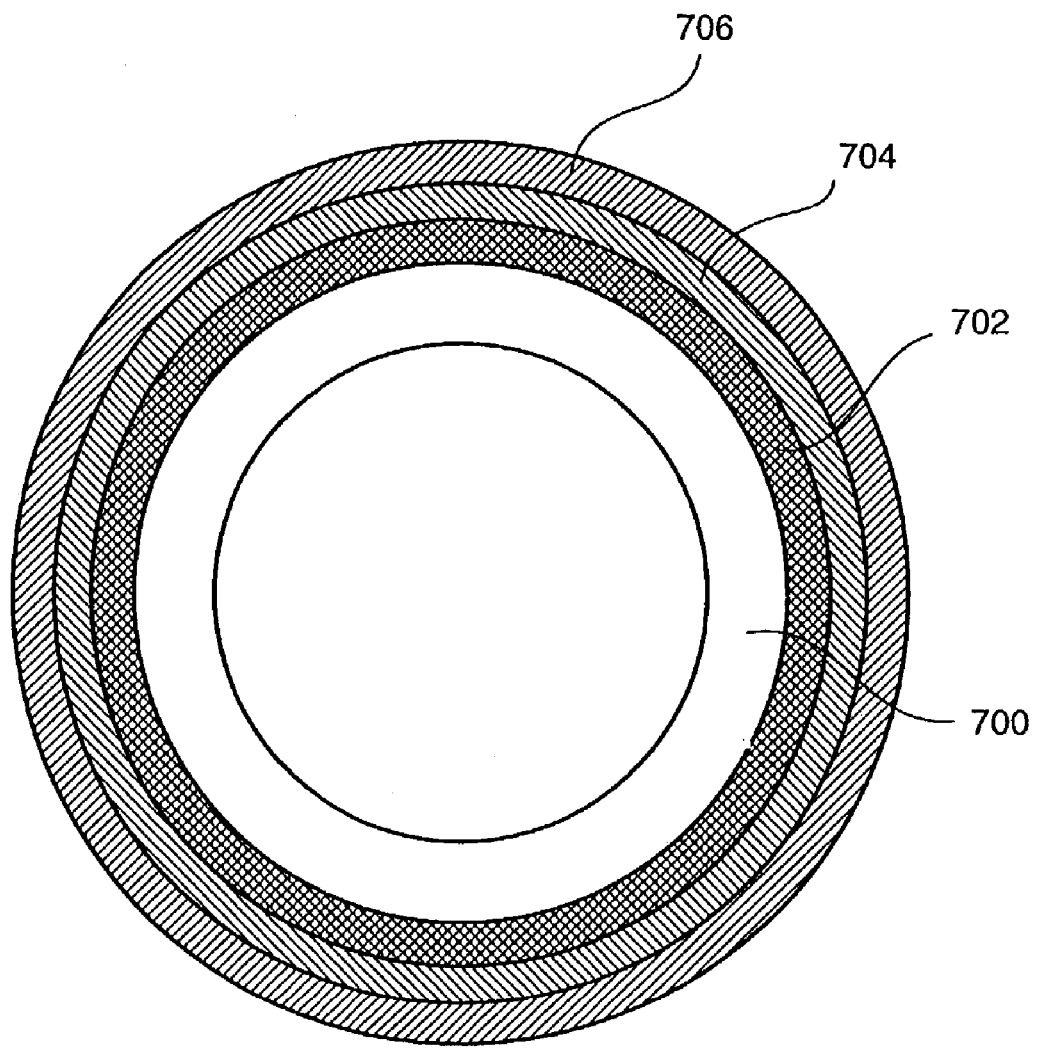
FIG. 14 is a schematic illustration of a cross section of a multiply-coated medical support device, constructed and operative in accordance with another embodiment of the disclosed technique.

Reference is now made to FIG. 14, which is a schematic illustration of a cross section of a multiply-coated medical support device, generally referenced 700, constructed and operative in accordance with another embodiment of the disclosed technique. Multiply-coated medical support device 700 includes a plurality of coatings 702, 704 and 706, which are overlaid one on top of the other. Coatings 702, 704 and 706 are different. The thickness of coatings 702, 704 and 706 can be either the same or different. Coatings 702, 704 and 706 are applied on the outer surface of multiply-coated medical support device 700. However, other coatings (not shown) can be applied also to the inner surface of the multiply-coated medical support device.

Figure 15:
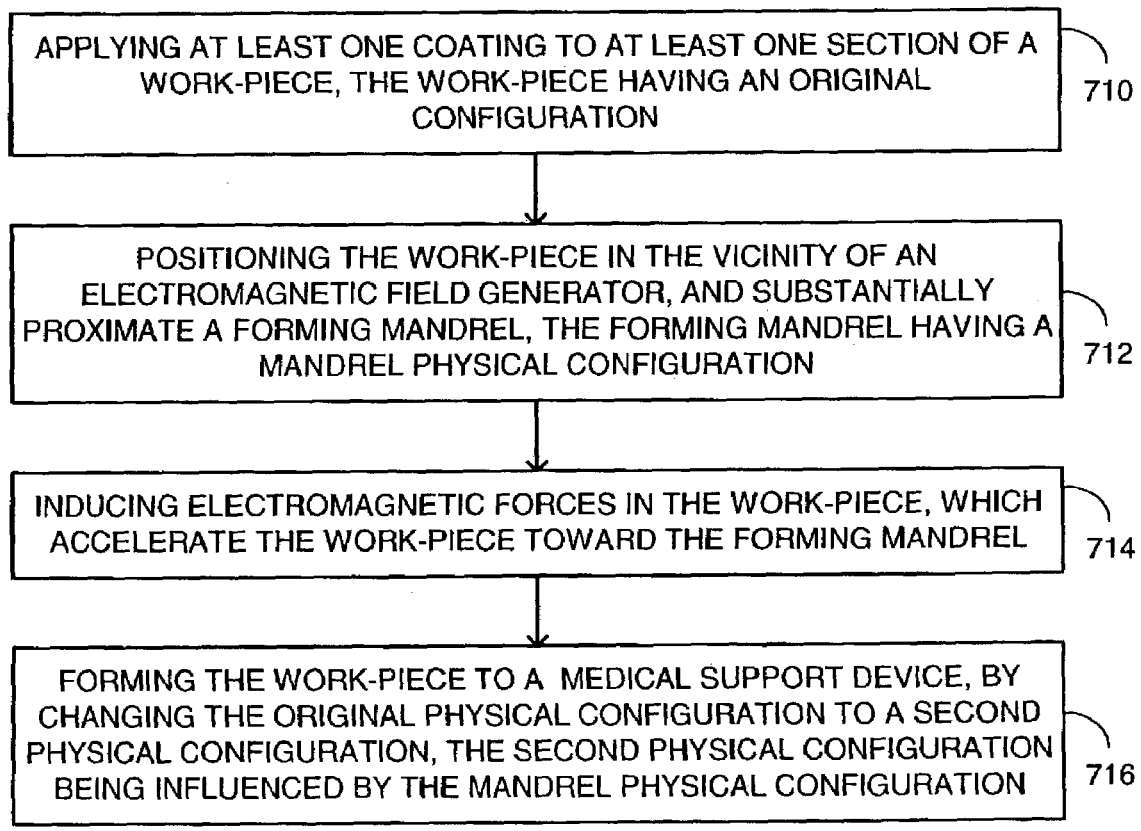
FIG. 15 is a schematic illustration of a method for constructing a coated medical support device, operative in accordance with a further embodiment of the disclosed technique.

Reference is now made to FIG. 15, which is a schematic illustration of a method for constructing a coated medical support device, operative in accordance with a further embodiment of the disclosed technique. In procedure 710, at least one coating is applied to at least one section of a work-piece, the work-piece having an original configuration. With reference to FIG. 11A, work-piece 582 is coated with coating 584, at a predetermined thickness, on a surface of work-piece 582. At this stage of the construction method, work-piece 582 is free of any holes (i.e., having the original configuration). Alternatively, different sections of the surface of work-piece 582 can be coated with different types of coatings at different thicknesses. Further alternatively, different sections of the other side of the work-piece can be coated with other coatings at different thicknesses.

In procedure 712, the work-piece is positioned in the vicinity of an electromagnetic field generator, and substantially proximate a forming mandrel, the forming mandrel having a mandrel physical configuration. With reference to FIG. 11B, coated work-piece 580 is positioned between forming coils 592 and 594 and mandrel 596 is positioned between forming coil 592 and coated work-piece 580. Mandrel 596 is provided with a plurality of holes 598 (i.e., having mandrel physical configuration). Forming coils 592 and 594, power source 586 and the energy storage capacitors form an electromagnetic field generator.

In procedure 714, electromagnetic forces are induced in the work-piece, which accelerate the work-piece toward the forming mandrel. With reference to FIG. 11B, the electromagnetic field generator (i.e., forming coils 592 and 594, the energy storage capacitors and power source 586), induce electromagnetic forces in coated work-piece 580, which in turn accelerate coated work-piece 580 toward mandrel 596.

In procedure 716, the work-piece is formed to a medical support device, by changing the original physical configuration to a second physical configuration, the second physical configuration being influenced by the mandrel physical configuration. With reference to FIG. 11C, the acceleration of coated work-piece 580 toward mandrel 596, causes a plurality of holes 600, substantially similar to holes 598, to be formed in coated work-piece 580. In this manner the physical configuration of coated work-piece 580 as in FIG. 11A (i.e., the original configuration), is changed to that of FIG. 11C (i.e., the second configuration).

It is noted that the second physical configuration of coated work-piece 580 is influenced by the physical configuration of mandrel 596. It is further noted that procedure 710 can be performed after procedure 716 (i.e., the work-piece is first formed and then coated).

It will be appreciated by persons skilled in the art that the disclosed technique is not limited to what has been particularly shown and described here in above. Rather the scope of the disclosed technique is defined only by the claims which follow.

The invention claimed is:

1. Method for producing a coated medical support device capable of insertion into the body, the method comprising the procedures of:

applying at least one coating to at least one section of a work-piece, said work-piece having an original configuration;

positioning said work-piece in the vicinity of an electromagnetic field generator, and substantially proximate a forming mandrel, said forming mandrel having a mandrel physical configuration;

inducing electromagnetic forces in said work-piece, which accelerate said work-piece toward said forming mandrel; and forming said work-piece to a medical support device, by changing said original physical configuration to a second physical configuration, said second physical configuration being influenced by said mandrel physical configuration.

2. The method according to claim 1, wherein said procedure of applying is performed after said procedure of forming.

3. The method according to claim 1, wherein said at least one coating comprises a plurality of coatings, and wherein a first one of said plurality of coatings is overlaid on a second one of said plurality of coatings.

4. The method according to claim 1, wherein said procedure of forming further comprises the procedure of forming a plurality of perforations in said work-piece.

5. The method according to claim 1, wherein said work-piece is substantially cylindrical.

6. The method according to claim 1, wherein said procedure of forming includes joining the edges of said work-piece.

7. The method according to claim 1, wherein at least one of said at least one section is located on one side of said work-piece and at least another of said at least one section is located on the other side of said work-piece.

8. The method according to claim 1, wherein said at least one section comprises a plurality of sections, and wherein in said procedure of applying, different coatings are applied to different sections of said plurality of sections.

9. The method according to claim 1, wherein said procedure of applying is performed by applying said at least one coating, at different thicknesses.

10. The method according to claim 1, wherein said work-piece is made of a material, selected from the list consisting of:

shape memory material;
super elastic material;
stainless steel;
alloy;
polymeric material; and
biocompatible material.

11. The method according to claim 1, wherein said at least one coating is a substance selected from the list consisting of:

sirolimus;
actinomycin D; N. O. donors;
dexamethasone;
heparin;
hirudin;
iloprost;
metallo-proteinase inhibitors;
platelet glycoprotein 2b/3a antagonist;
genes;
cells;
silicone;
silicone carbide;
phosphorylcholine;
carbide;
carbofilm.TM.;
titanium-nitride-oxide;
expandable polytetrafluorethylene membrane;
gold; and
polyethylene oxide.

* * * * *